United States Patent [19]

Li et al.

[11] Patent Number: 5,783,554

[45] Date of Patent: Jul. 21, 1998

[54] CLEANING COMPOSITIONS CONTAINING ANIONIC SURFACTANTS HAVING MULTIPLE HYDROPHOBIC AND HYDROPHILIC GROUPS

[75] Inventors: Ji Li, East Windsor; Manilal Dahanayake, Princeton Junction; Robert Lee Reierson, Cranbury; David James Tracy, Plainsboro, all of N.J.

[73] Assignee: Rhodia Inc., Cranbury, N.J.

[21] Appl. No.: 886,105

[22] Filed: Jun. 30, 1997

Related U.S. Application Data

[62] Division of Ser. No. 292,907, Aug. 19, 1994, Pat. No. 5,643,864.

[51] Int. Cl.$^6$ .................. C11D 1/04; C11D 1/28; C11D 1/34; C11D 1/66

[52] U.S. Cl. .................. 510/488; 510/469; 510/494; 510/495; 510/501; 510/426; 510/427; 510/431; 510/433

[58] Field of Search .................. 510/501, 499, 510/506, 494, 495, 469, 488

[56] References Cited

U.S. PATENT DOCUMENTS

| | | | |
|---|---|---|---|
| 4,721,512 | 1/1988 | Toepfl et al. | 8/188 |
| 4,728,337 | 3/1988 | Abel et al. | 8/606 |
| 4,906,413 | 3/1990 | Toepfl et al. | 260/404.5 |
| 5,160,450 | 11/1992 | Okahara et al. | 252/174.21 |

FOREIGN PATENT DOCUMENTS

| | | |
|---|---|---|
| 344344 A1 | 12/1989 | European Pat. Off. . |
| 697245 A1 | 2/1996 | European Pat. Off. . |
| 1149140 | 4/1969 | United Kingdom . |

*Primary Examiner*—Margaret Einsmann
*Assistant Examiner*—John R. Hardee
*Attorney, Agent, or Firm*—Craig M. Bell

[57] ABSTRACT

According to the invention, an improved class of surfactants having improved surfactant properties characterized as mild and environmentally safe have been provided comprising compounds of the formula:

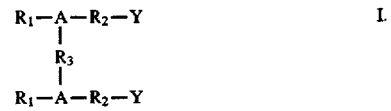

The anionic surfactants of the invention have at least two hydrophobic chains and at least two hydrophilic groups per molecule and are useful as emulsifiers, detergents, dispersant and solubilizing agents.

22 Claims, No Drawings

CLEANING COMPOSITIONS CONTAINING ANIONIC SURFACTANTS HAVING MULTIPLE HYDROPHOBIC AND HYDROPHILIC GROUPS

This application is a divisional of U.S. Pat. No. 08/292,907 filed Aug. 19, 1994, now U.S. Pat. No. 5,643,864.

This invention relates to a novel group of anionic surfactants having at least two hydrophobic moieties and at least two hydrophilic groups per molecule useful as emulsifiers, detergents, dispersants, hydrotropes, wetting agents, corrosion inhibitors and solubilizing agents.

BACKGROUND OF THE INVENTION

Surfactants are well known materials which can be generally described as having a hydrophobic moiety and a hydrophilic group per molecule. A wide variety of these materials are known and are classified as anionic, cationic, nonionic and amphoteric. They are well known to have numerous uses such as emulsifiers, detergents, dispersants and solubilizing agents in the fields of cosmetics, textile treatment, industrial and personal cleaning preparations, corrosion inhibitors and the like.

Anionic surfactants carry a negative charge on the hydrophilic portion, usually in the form of a carboxylate, phosphate, sulfate or sulfonate. These surfactants find use in emulsion polymerization as well as in agricultural chemicals, personal care and household products, industrial and institutional cleaners. They function as emulsifiers, cleaners, wetting agents, foaming and frothing agents such as for shampoos, car washes, carpet shampoos, hand dishwashing, latex foaming, oil recovery and other industrial uses.

Surfactants generally are compounds having one hydrophilic group and one hydrophobic moiety. Recently, a group of compounds having two hydrophobic moieties and two hydrophilic groups have been introduced. These have become known as "Gemini surfactants" in the literature (*Chemtech*, March 1993, pp 30–33), and *J. American Chemical Soc.*, 115, 10083–10090, (1993) and the references cited therein. Since their introduction, cationic and anionic "Gemini surfactants" have been disclosed. Other surfactant compounds having two hydrophilic groups and two hydrophobic moieties have been disclosed but not referred to as Gemini surfactants.

Sulfate, phosphate and carboxylate surfactants are currently disclosed in the Literature (See JAOCS 67, 459 (1990); JAOCS 68, 268 (1991) JAOCS 68, 539 (1991); and JAOCS 69, 626 (1992). In each case a secondary hydroxyl is sulfated, carboxylated, or phosphated.

Secondary hydroxyl's phosphate poorly in that phosphoric anhydride leads to olefin production (dehydration) while polyphosphoric acid results in high levels of phosphoric acid and unphosphated material. The present invention results in compounds which are characterized by primary hydroxyl groups which can more efficiently be functionalized.

Similarly, sulfation can also lead to dehydration by-products. Carboxymethylation of secondary hydroxyl groups is also difficult resulting in low yields.

One author [JACS 115, 10,083 (1993) and JACS 113, 1451 (1991)] prepares a phosphate on a primary hydroxyl group. But in these references, it is necessary to utilize mixed alcohols to incorporate a hydrophobe into the molecule. This leads to the production of mixed diphosphate, a necessary outgrowth of using the mixed alcohols. This difficulty is eliminated in the present invention. In addition, high monoalkylphosphates as well as diphosphates can be prepared according to the present invention.

Due to the need for new and more effective and efficient surfactants, as well as the need for mild surfactants which are biologically compatible in an ecologically sensitive environment as well as the need for more effective and efficient surfactants, effort has been made to develop a new class of compounds, which demonstrate improved surface-active properties that are further characterized as mild, and environmentally benign.

SUMMARY OF THE INVENTION

According to the invention, an improved class of anionic surfactants having improved surfactant properties characterized as mild and environmentally benign have been provided comprising compounds of the formula:

I.

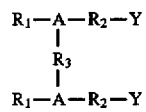

wherein $R_1$ can independently be alkyl, hydroxy substituted or perfluorinated alkyl of from about 5 to about 22 carbon atoms or $R_4$—B—$R_5$ wherein $R_4$ can be alkyl or hydroxy substituted or perfluorinated alkyl of from 1 to about 22 carbon atoms, $R_5$ can be alkylene of from 1 to about 12 carbon atoms and the hydroxy substituted derivatives thereof;

B can be an amide group [—C(O)N($R_6$)— or —N($R_6$)C(O)—], a carboxyl group [—C(O)—O— or —OC(O)—], a carbonyl group or a polyether group [—O($R_7$—O)$_x$—], wherein $R_6$ independently represents lower alkyl or hydroxy substituted alkyl from 1 to about 6 carbons or hydrogen and $R_7$ independently represents about $C_2$ to about $C_4$ alkyl with x being a number between 1 and 20;

$R_2$ can independently be $C_1$ to about $C_{10}$ alkylene and the hydroxy substituted derivatives thereof, an amide group [—C(O)N($R_6$)—], a polyether group [—O($R_7$—O)$_x$—] or $R_8$—$D_1$—$R_8$ wherein R6 and $R_7$ are as defined hereinbefore and $R_8$ can independently be $C_1$ to about $C_6$ alkylene and the hydroxy substituted derivatives thereof and $D_1$ represents —O—, —S—, an amide group [—C(O)N($R_6$)—] or —N($R_9$)— wherein $R_9$ independently represents $C_1$ to about $C_{12}$ alkyl and the hydroxy substituted derivatives thereof or hydrogen;

$R_3$ can independently be alkylene or alkylaryl of 1 to about 10 carbon atoms and the hydroxy substituted derivatives thereof or $R_{10}$—$D_2$—$R_{10}$ wherein $R_{10}$ can independently be alkylene of from 1 to about 6 carbon atoms and the hydroxy substituted derivatives thereof as well as aryl illustrated by phenylene, diphenylene and sulphonyldiphenylene, and $D_2$ represents —O—, —S—, —$SO_2$—, a carbonyl group, a polyether group [—O($R_7$—O)$_x$—],—($R_{11}$)$_y$[N($R_{11}$)]$_z$ — or aryl wherein $R_{11}$ represents alkyl of from 1 to about 12 carbon atoms and the hydroxy substituted derivatives thereof or hydrogen, $R_7$ being as defined hereinbefore with x being a number between 1 and 20 and y and z are independantly numbers from 1 to about 4;

"A" independently represents —$CR_6$=or —N=with the proviso that when "A" is —N=then $R_1$ is $R_4$—B—$R_5$; and Y independently represents hydrogen, —SO₃H, —OSO₃H, —OP(O)(OH)₂, —P(O)(OH)₂, —COOH, —CO₂—C₆H₄—SO₃H and salts thereof, the pH of use being sufficent to form an anionic surfactant, e.g., pH of about 11.

When compared to the corresponding conventional anionic surfactants, the novel compound of the invention show two unexpected surface active properties; unusually low critical micelle concentration (CMC) and pC-20 values in aqueous media. These properties are a measure of the tendency of the surfactant to form micelles and adsorb at the interface respectfully, and consequently, to reduce surface tension.

Preferably $R_3$ is alkyl or perfluoroalkyl of from about $C_6$ to about $C_{18}$ carbon atoms, and the hydroxy substituted derivatives thereof or $R_8$—$D_1$—$R_8$ wherein $R_8$ can independently be alkylene of from 1 to about 6 carbon atoms. B is preferably an amide group. Preferably, $R_3$ is independently lower alkylene of from 1 to about 4 carbon atoms and the hydroxy substituted derivatives thereof. $R_4$ is preferably lower alkylene and the hydroxy substituted derivatives thereof of from 1 to 10 carbon atoms. Y is preferably carboxyl, sulfate, phosphate and salts thereof. The salts in Formula I can be an alkali metal salt (Na, K) an alkaline earth metal salt (Mg, Ca), an ammonium salt, or an organic base salt. The organic base salt can be illustrated by monoethanolamine, diethanolamine, triethanolamine, triethylamine, trimethylamine, N-hydroxyethyl morpholine and the like.

More specifically, the compounds of the present invention comprise:

II.

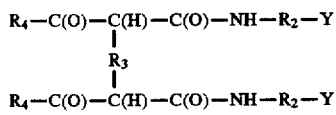

III.

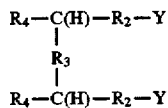

IV.

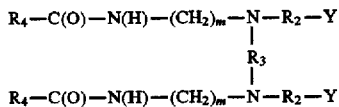

V.

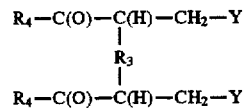

wherein $R_2$, $R_3$, $R_4$, and Y are as defined hereinbefore, and m is a number between about 2 and about 10.

In compounds II, III, and V, $R_3$ is preferably —O—$R_8$—O, and in compound IV, $R_3$ is preferably —C(O)—$R_{10}$—C(O)—. In compound V, $R_3$ is more preferably —O—$C_4H_8$—O—. In compound III, one of the preferred $R_2$ groups is an amide group and more preferably where both $R_2$ groups are amide groups.

Uniquely, the invention provides anionic surfactants having a primary hydroxyl group which can be readily phosphated, sulfonated or carboxylated by standard techniques.

In addition to new compounds, the invention also discloses novel synergistic compositions when the compounds of the invention are blended with other surfactants.

DETAILED DESCRIPTION OF THE INVENTION

While the compounds of the invention can be prepared by a variety of synthetic routes, it has been found that they can be produced particularly effectively by a novel process disclosed and claimed in copending application "Amphoteric Surfactants having Multiple Hydrophobic and Hydrophilic Groups", Ser. No. 08/292,993 (Attorney's Docket No. RD 94015) filed coextensively herewith wherein a polyamine reactant having at least four amino groups of which two are terminal primary amine groups is reacted with an acylating agent such as a carboxylic acid, ester, and the naturally occurring triglyceride esters thereof or acid chlorides thereof in an amount sufficient to provide at least about 1.8 fatty acid groups [$R_1C(O)$—] per polyamine to provide a bisimidazoline, of the formula:

VI.

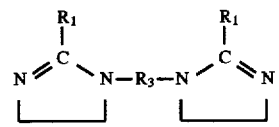

This reaction proceeds effectively at elevated temperatures (about 100° C.–250° C.) with continuous removal, such as by distillation, of the resulting condensate ($H_2O$) during the course of the reaction.

The progress of the reaction can be monitored by the amount of water recovered in the distillate. Two moles of water are generated for each imidazoline ring formed, one mole in the condensation reaction and one mole in the cyclodehydration reaction to form the imidazoline, hence double that for the bisimidazoline compounds. The process can be carried out with or without a catalyst, at atmospheric, reduced or super atmospheric pressure. The use of excess amine can result in undesirable by-products and is not recommended. Stoichiometric excess of fatty acid, ester, chloride or triglyceride can be used but is less desirable as it may require the need of a purification step to remove the excess.

In the compounds of Formula I, $R_1$ and $R_4$ can be derived from fatty acids, esters and triglycerides or the acid chlorides thereof from synthetic and natural sources which will generally contain mixtures of different carbon chain length saturated and unsaturated aliphatic radicals. The natural sources can be illustrated by coconut oil (preferred) or similar natural oil sources such as palm kernel oil, palm oil, soya oil, rapeseed oil, castor oil or animal fat sources such as herring oil and beef tallow. Generally, the fatty acids from natural sources in the form of the fatty acid or the triglyceride oil can be a mixture of alkyl radicals containing from about 5 to about 22 carbon atoms. In a more preferred material, the mixture of alkyl radicals can be derived from a saturated portion of coconut oil (from about 6 to about 18 carbon atoms) or similar natural vegetable oil. These ranges cover about 90% of the carbon chains in the compound. Since these fatty acids are derived from natural sources, they can contain small amounts of other carbon chains. Illustrative of the fatty acids in these oils are caprylic($C_8$), capric (10), lauric (12), myristic(14), palmitic(16), stearic (18), oleic (18, monounsaturated), linoleic (18, diunsaturated), linolenic (18, triunsaturated), ricinoleic (18, monounsaturated), arachidic (20), gadolic(20, monounsaturated), behenic (22) and erucic(22). These fatty acids can be used per se, as concentrated cuts or as fractionations of natural source acids. The fatty acids with even numbered carbon chain lengths are given as illustrative though the odd numbered fatty acids can also be used. In addition, single carboxylic acids, e.g., lauric acid, or other cuts, as suited for the particular application, may be used. Examples of acids derived from synthetic sources that can be used include 2-ethylhexanoic acid, pelargonic acid and the like.

The polyamine reactant has at least four amino groups of which two are terminal primary amine groups. The preferred polyamine is illustrated by triethylene tetramine (TETA). Other polyamines such as tetraethylenepentamine and others that would be obvious to one of skill in the art can also be used. The amine reactant can be defined by the structure:

$H_2NCH_2CH_2NH$—$R_3$—$NHCH_2CH_2NH_2$  VII.

wherein $R_3$ is generally alkyl and aminoalkyl. The improved method of the invention will be illustrated with TETA but this is not intended to limit the invention to that starting material.

TETA is reacted with a sufficient amount of fatty acid to provide at least about 1.8 fatty acid groups, preferably from about 1.9 to about 2.5 fatty acid groups, per molecule of polyamine to provide the bisimidazoline compound as in Formula VI wherein $R_3$ is ethylene.

The bisimidazoline compound, when hydrolyzed under basic pH conditions will selectively form a bisamidoamine compound of Formula VIII:

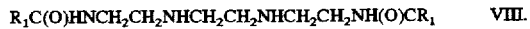

$R_1C(O)HNCH_2CH_2NHCH_2CH_2NHCH_2CH_2NH(O)CR_1$  VIII.

This compound can be generically represented by compounds of the formula:

$R_1C(O)HNCH_2CH_2NH$—$R_3$—$NHCH_2CH_2NH(O)CR_1$  IX.

where $R_3$ is generally alkyl or aminoalkyl.

The bisamidoamine compound (Compounds of Formula VIII or IX) can then be reacted with an alkylating agent to prepare the bisanionic compounds of the invention as defined in Formula I such as an organic compound with a reactive halogen illustrated by chloroacetic acid, its esters or salts; an active vinyl compound, which undergoes Michael addition, illustrated by methyl acrylate or sodium vinyl sulfonate; or electrophiles such as propane sultone or sodium, 3-chloro-2-hydroxypropyl sulfonate and the like.

For alkylation conditions and commonly used alkylating agents, see Amphoteric Surfactants Vol. 12, Ed. B. R. Bluestein and C. L. Hilton, *Surfactant Science Series* 1982, pg. 17 and references cited therein, the disclosures of which are incorporated herein by reference.

A second mode of synthesis includes the steps of forming a single imidazoline such as from ethylenediamine and a fatty acid, ester, chloride or triglyceride. The fatty acids, esters, chloride or triglycerides thereof can be reacted with α,β-diamines in substantially equimolar quantities at temperatures ranging from about 150° to 250° C. with continuous removal of the resulting condensate ($H_2O$). The process can be carried out with excess amine, with or without a catalyst, at atmospheric, reduced or super atmospheric pressure.

The imidazoline can then be reacted with any difunctional compound that will join two of the imidazoline rings to form the bisimidazoline compound of the invention. These can be illustrated by any reactive dihalide, e.g., alpha, omega-dihalobutane, alpha, beta-dihaloethane, alpha, alpha'-dihaloparaxylene, diglycidyl ethers, diepoxides as well as epihalohydrins such as epichlorohydrin and the like.

In addition to alkyl and aminoalkyl groups contained in the examples of the poylamines given above, $R_2$ can thus be further illustrated by hydroxy—substituted alkyl such as —$CH_2CHOHCH_2$; an ether such as —$CH_2CH_2OCH_2CH_2$ or an alkylarylalkyl such as —$CH_2$—$C_6H_4$—$CH_2$—.

For reaction conditions generally, see JACS 67, 1581 (1945); U.S. Pat. Nos. 1,790,042; 1,845,403; JCS 1666 (1931), the disclosures of which are incorporated herein by reference. The reaction conditions must be such as to maintain the imidazoline ring structures.

The bisimidazoline compound, represented by Formula VI, when hydrolyzed under basic pH conditions will form the amidoamine compound as represented by Formula IX where $R_3$ is —$CH_2CH(OH)CH_2$— which can be reacted with an alkylating agent to form the bisanionic compounds represented by Formula I.

The compounds of the invention where "A" is carbon can be produced from beta-carbonyl compounds by the reaction of a active hydrogen site with a dihalo compound (See R. C. Fuson and H. R. Snyder Organic Chemistry, 2nd edition, pages 322 and 324, the disclosure of which is incorporated herein by reference.

The compounds of the invention where "A" is carbon cvan also be produced by condensation of the beta haloacid [See *J. Chem. Soc. Trans.*, 1888 (1905), Chem Ber 24, 2388 (1891)], the disclosure of which is incorporated herein by reference, with nucleophiles such as dihydroxy compounds, e.g., hydroquinones (See R. C. Fuson and H. R. Snyder Organic Chemistry, 2nd edition, page 65, the disclosure of which is incorporated herein by reference.

The compounds of the invention can also be produced by reducing the carboxy groups of the following compounds to alcohols:

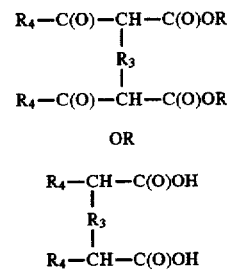

Alternatively, the above compounds can be reacted with an amino alcohol of the formula $NH_2$—R—OH to form compounds of Formula II. These compounds are characterized by primary hydroxyl groups which can be easily phosphated or sulfated by normal methods.

The compounds of the invention can also be prepared from anionic intermediates by reacting a hydroxyl terminated polyamine with a fatty acid halide as per the following representation:

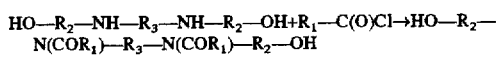

HO—$R_2$—NH—$R_3$—NH—$R_2$—OH+$R_1$—C(O)Cl→HO—$R_2$—N(COR$_1$)—$R_3$—N(COR$_1$)—$R_2$—OH

This compound can be reacted with a sulfating or phosphating agent such as sulfur trioxide, sulfamic acid, cholrosulfonic acid or phosphoric anhydride to form the compounds of the invention (Sulfation techniques are discussed in Surfactant Science Series, Vol 7, Part 1, S. Shore & D. Berger, page 135, the disclosure of which is incorporated herein by reference. For phosphating review see Surfactant Science Series, Vol 7, Part II, E. Jungermann & H. Silbrtman, page 495, the disclosure of which is incorporated herein by reference.) The compounds of the invention can also be prepared by reacting an amidoamino alcohol compound of the formula $R_4C(O)NH-R_5-NH-R_2-OH$ with a dicarboxylic acid or acid chloride as per the following representation:

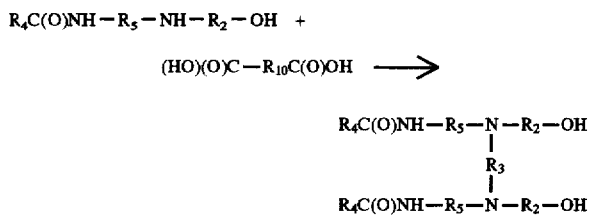

wherein $R_3$ is $-C(O)-R_{10}-C(O)-$.

Since the surfactants of the invention exhibit an extremely low critical micelle concentration (CMC) as compared with conventional surface-active agents because of the presence of two hydrophobic moieties and two hydrophilic groups in their molecule and since they are able to fully reduce surface tension and are highly soluble in water, the surfactants of the invention are extremely effective in aqueous solution at low concentrations. While the surfactants of the invention can be used in any amount needed for the particular application which can be easily determined by a skilled artisan without undue experimentation.

The surfactants of the invention can be used alone as the essential hydrotrope component.

It has also been unexpectedly found that blends of the compounds of the invention with certain conventional well known anionic, nonionic, cationic and amphoteric surfactants provide results beyond that expected and therefore synergistic that can be demonstrated in relation to critical micelle concentration and surface tension reducing ability.

Examples of the nonionic surfactants used herein include fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono- or diamides and alkylamine oxides. Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives. Examples of the cationic surfactants used herein include alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants. Examples of the amphoteric surfactants used herein include amino acid, betaine, sultaine, phosphobetaines, imidazoline type amphoteric surfactants, soybean phospholipid, and yolk lecithin.

In addition to the foregoing surfactants, any of commonly used auxiliary additives may be added to the surfactants of the invention or blends thereof with other surfactants as disclosed herein. Such auxiliary additives may be added to the surfactants of the invention on use. Such auxiliary additives may be suitably chosen for a desired composition and generally include inorganic salts such as Glauber salt and common salt, builders, humectants, solubilizing agents, Uv absorbers, softeners, chelating agents, and viscosity modifiers.

The anionic surfactants of the invention are extremely mild and non-irritating to both eyes and skin. They also exhibit enhanced wetting speed, greater surface tension reduction, high foaming and foam stabilization properties, low toxicity, and excellent compatibility with other anionic, ionic and nonionic surfactants. The products of the invention are stable over a wide pH range and are biodegradable. These properties make these surfactants adaptable for use in products ranging from cosmetics to industrial applications and are usable wherever anionic surfactants have found use. These products are particularly useful for non-irritating shampoos, including baby shampoos, body shampoos including bubble baths, bar soaps, bath gels, hair conditioning gels, lotions, skin creams and lotions, make up removal creams and lotions, liquid detergents, dish detergents and other washing and cosmetic products that contact the skin. The surfactants of the invention can also find use as hard surface cleaners including cars, dishes, toilets, floors, and the like; laundry detergents and soaps, metal working aids and the like.

Examples of the present invention are given below by way of illustration and not by way of limitation. All parts and percents are by weight.

EXAMPLE 1

Synthesis of Ethylene bis-laurimidazoline of Formula VII where $R_1$ is $C_{11}H_{23}$.

To a 500 mL, three-necked, round bottom flask equipped with a stirrer, temperature controller, and a Barrett distilling receiver with a condenser on top, was added 46.7 g (0.25 mol) triethylenetetramine hydrate (average 2.1 to 2.2 moles water by Karl Fisher Analysis), 104 g (0.52 mol) lauric acid and 100 mL toluene. The Barrett distilling receiver was filled with toluene. The reaction mixture was gently heated with stirring to reflux (120°–130° C.) and water collection was initiated.

The progress of the reaction was followed by monitoring the amount of water collected as the toluene azeotrope. The first 20 mL which was collected in the first three hours of the reflux period indicated that the reaction was 70% complete.

The reaction temperature was slowly raised to 160°–180° C. during the 12 to 16th hour of reaction by stripping the reactor-contained toluene through the Barrett distillation receiver. The progress of the reaction was also determined by gas chromatography. The disappearance of the peak corresponding to the diamide indicated completion of the condensation reaction.

After 16 hours of reaction, the reaction was stopped, as 27.2 mL (99% of the theoretical 28 mL) of water had been collected. Gas chromatography showed that the 126 grams of product obtained contained greater than 96% of the desired ethylene bis-laurimidazoline (VIII).

The product was recrystallized from $CHCl_3$ for structure characterization and identification. The $^1H$ and $^{13}C$ NMR, IR, and Mass Spectra were recorded and the results agreed with the postulated structure.

EXAMPLE 2

Synthesis of N,N'-bis(2-lauramidoethyl) ethylenediamine of Formula IX wherein $R_1$ is $C_{11}H_{23}$.

To a 100 mL three-necked round bottom flask equipped with magnetic stirrer-bar, temperature control, a condenser and a pH probe connected with a readout, was added a solution of 0.2 g of NaOH in 2 mL water and 4.74 g (10 mmol) of ethylene bis-laurimidazoline prepared by the process in Example 1. The reaction mixture was then stirred, heated and maintained at 85°–95° C. for 6–8 hours until the pH value of the reaction mixture remained unchanged. Analysis by gas chromatography indicated less than 5% of the starting material (some of the starting material shown by GC is caused by cyclization of the compound of Formula IX in GC injection port). The reaction was stopped at this point to avoid further hydrolysis of the desired bisamidoamine compound of Formula IX. The mixture was cooled to 60° C. and diluted with 2 mL tetrahydrofuran. The crude product precipitated as a white solid as the liquid cooled to room temperature. Recrystallization from 4 mL of fresh tetrahydrofuran produced 4.1 g (80% yield) of the N,N' bis (2-lauramidoethyl) ethylenediamine, mp. 110°–112° C. The $^1H$ and $^{13}C$ NMR, DEPT$^{13}C$ NMR, IR and Mass Spectra were recorded and agreed with the proposed structure.

EXAMPLE 3

Synthesis of the N,N'-bis(2-lauramidoethyl) ethylenediamine-N,N' di(sodium propionate), compound of Formula IV wherein $R_4$ is $C_{11}H_{23}$, m is 2, $R_2$ and $R_3$ is are ethylene and Y is $CO_2Na$.

To a 250 mL three-necked, round bottom flask equipped with a magnetic stirring bar, temperature control, and a condenser was added 5.9 g (10 mmol) of N,N'-bis(2-lauramidoethyl) ethylenediamine of Example 2 (greater than 98% purity) and 8.6 g (100 mmol) of methyl acrylate. The reaction mixture was then refluxed at 80° C. for 13 hours with stirring. After stripping out excess methyl acrylate under vacuum, 6.35 g (100% yield) of white waxy solid product was obtained. Gas chromatography showed that the waxy solid contained more than 98% of the desired di-(methyl ester) of the title compound which was characterized by $^1H$ and $^{13}C$ NMR.

To another 250 mL, three necked, round bottom flask equipped with a magnetic stirrer bar and temperature control, was added 0.7 g NaOH in 23 mL of water. The reaction mixture was heated to 45° to 55° C. At this temperature, 5.6 g of the white, waxy dimethyl ester product obtained above was added in one portion. The reaction mixture was stirred at 45° to 55° C. for 5 to 6 hours.

After completion of the hydrolysis, the contents were transferred to a beaker which was then placed in a heated water bath. Evaporation of the water left 5.7 grams of the amphoteric surfactant of the title compound, Formula IV, as a white solid. The $^1H$ and $^{13}C$ NMR were recorded and agreed with the proposed structure.

EXAMPLE 4

Synthesis of N,N' bis(2-lauramidoethyl) ethylenediamine-N,N'-di(sodium 2-hydroxy-3 propyl sulfonate) compound of Formula IV wherein $R_1$ is $C_1H_{23}$, m is 2, $R_2$ is $CH_2CH(OH)CH_2$ $R_3$ is ethylene, and Y is $SO_3Na$.

To a 250 mL, three-necked, round-bottom flask equipped with a mechanical stirrer bar, thermometer and a condenser, were added 5.7 g (60 mmol) of sodium metabisulfite, 60 mg of 50% NaOH and 33.9 g of water. The reaction mixture was heated to 50°–60° C. and epichlorohydrin (5.55 g, 60 mmol) was added over a period of about an hour. The reaction mixture was then heated with stirring at 60°–65° C. for one hour, after which 10.3 g (20 mmol) of the bisamidoamine compound of Formula IX where $R_3$ is ethylene prepared according to the process of Example 2, 12 g of isopropyl alcohol and 44 g of water were added. The reaction mixture was heated to reflux, and 4.8 g (60 mmol) of 50% NaOH was added over a period of 3 hours.

About 6 mL of alcohol/water was then distilled out and replaced with 8 mL of water. After heating to reflux for two hours, another 10 mL of water was added and reflux continued for another hour.

The product was evaporated to dryness, extracted with tetrahydrofuran, and the solvent evaporated. Yield: 15 g, 60% yield. Structure confirmed by $^{13}C$ NMR.

EXAMPLE 5

Synthesis of N,N' bis(2-lauramidoethyl) ethylenediamine-N,N' di(sodium acetate) compound of Formula IV wherein $R_1$ is $C_{11}H_{13}$, m is 2, $R_3$ is ethylene, $R_2$ is methylene and Y is $CO_2Na$.

To a 500 mL three-necked, round bottom flask equipped with a mechanical stirrer bar, thermometer and a condenser, 28.4 g (300 mmol) of monochloroacetic acid and 200 mL of water were added. The stirred solution was cooled in an ice bath during the dropwise addition of 26.2 g (300 mmol) 50% NaOH to maintain the temperature below 25° C. The ice bath was removed, and 61.5 g (100 mmol) of bisamidoamine of Formula X prepared according to Example 2 and 50 g of isopropyl alcohol was added and the liquor was heated to 75° C. The pH was maintained at 9–10.5 by addition of 21.8 g (270 mmol) 50% NaOH at 75° C. over the 5 hour reaction period. The reaction mixture was then heated to 85° C. and 42 mL of IPA/water was distilled out and replaced with 42 ml of water. The reaction was run another 12 hours at 90° C., until the reaction was complete as indicated by the free to total chloride ratio of near unity (>0.99~99% conversion).

The solvent was allowed to evaporate overnight in a crystallizing dish in the hood. Drying was completed in a vacuum oven at 70° C. for 2 hours, to give 74 g of the desired product. (81% of theoretical) The structure was confirmed by the $^{13}C$ NMR spectrum.

EXAMPLE 6

Preparation of $C_8H_{17}NHC(O)CH_2CH_2N(CH_2CH_2OH)CH_2CH_2N$ —$(CH_2CH_2OH)$ $CH_2CH_2C(O)NHC_8H_{17}$ Step 1. Preparation of $CH_3OC(O)CH_2CH_2N$ $(CH_2CH_2OH)CH_2CH_2$ N—$(CH_2CH_2OH)CH_2CH_2C(O)OCH_3$.

A mixture of 30 grams (0.20 mol) of bis(2-hydroxyethyl) ethylenediamine and 250 mL of toluene were added to a 500 mL three necked flask equipped with a thermometer, condenser, and addition funnel and heated with stirring. At 80° C., 34.4 grams (0.40 mol) of methyl acrylate was added dropwise over a period of 2 hours. A clear solution was obtained at the end of the addition. The reaction mixture was held at 80° C. with stirring for an additional 8 hours to allow the reaction to proceed to completion. Toluene was removed under vacuum to obtain 46.7 grams of product in 99% yield. The $^{13}C$ NMR agreed with the structure assignment.

Step 2. Preparation of $C_8H_{17}NHC(O)CH_2CH_2N$ $(CH_2CH_2OH)$ $CH_2CH_2$ N—$(CH_2CH_2OH)CH_2CH_2C(O)NHC_8H_{17}$ 46.8 grams (0.20 mol) of the compound prepared above and 46.5 grams (0.20 mol) of n-octyl amine were heated in a 150 mL flask at 150° C. under vacuum for 20 hours to yield the desired compound. The reaction progress was monitored by GC and $^{13}$C NMR.

The hydroxy terminated compound as prepared in this example and as disclosed in this application can be phosphated by standard phosphating techniques employing phosphoric anhydride to yield the corresponding phosphate ester. Care is to be taken to avoid joining two of the anionic surfactnat molecules by forming a diphosphate. High di-(monoalkyl phosphates), the preferred species, can be prepared by the processes described in the copending patent applications of R. L. Reierson, U.S. application Ser. Nos. 08/220,069 and 08/220,339 filed Mar. 30, 1994, the disclosures of which are incorporated herein by reference.

EXAMPLE 7

Preparation of Surfactant Compound IV wherein $R_1$ is $C_7H_{15}$.

Preparation of bisimidazoline compound VIII wherein $R_1$ is $C_7H_{15}$.

The procedure of Example 1 is repeated using 100 grams (0.538 moles) of TETA hydrate, 154.9 grams (1.076 moles) of octanoic acid and 100 ml of toluene.

Preparation of bisamidoamine Compound IX wherein $R_1$ is $C_7H_{15}$.

The procedure of Example 2 was followed using a 500 ml 3 necked round-bottom flask, 145 grams (0.4 moles) of bisimidazoline as prepared above, 4 grams of 50% NaOH and 4 ml of water. Reaction time was 4 hours. The product was recrystallized from 80 ml of tetrahydrofuran and 200 ml water. The yield was 80 grams (42% yield) and the structure was confirmed by $_{13}$C NMR.

Synthesis of surfactant Compound IV wherein $R_1$ is $C_7H_{15}$

To a 500 ml four-necked round-bottom flask equipped with a mechanical stirrer, thermometer and condenser was added 64.0 g (0.16 moles) bisamidoamine as prepared above and 62 g of toluene and heated to 75°–85° C.

55.4 g. (0.64 moles) of methyl acrylate was added dropwise over a period of one hour. Maintain at 80°–85° C. for 16 hours. Strip excess toluene and methyl acrylate. $^{13}$C NMR confirms structure and shows about 90% product.

To the above flask was added 360 ml of water and 11.2 g (0.14 moles) of 50% NaOH and heated to 93°–97° was another 11.2 g (0.14 moles) of 50% NaOH was added incrementally while maintaining the pH at 9.0–10.0. Total reaction time was 6 hours. The reaction mixture was placed in an evaporating dish and evaporate to dryness at 60°–80° C. Finish off in vacuum oven. Extract with THF for 4 hours. Air dry to remove THF, and finish off in vacuum oven. Yield 45.5 g. % yield 49.2%. Structure confirmed by $^{13}$C NMR.

Surface Properties

The surfactants of the invention were measured for critical micelle concentration and surface tension reducing ability. The test methods utilized are described as follows:

Critical Micelle Concentration (CMC)

Aqueous solutions of a surfactant were prepared at varying concentrations. The surface tension at 20° C. was measured by the Wilhelmy plate method and plotted vs. the logarithm of the concentration. The critical micelle concentration was determined as the value at which the slope of the line changed abruptly.

Surface Tension Reducing Ability (gamma CMC)

The surface tension reducing ability was determined from the surface tension at the critical micelle concentration.

Surface tension measurements were made for each of the referenced surfactants, using a Kruss K-12 Tensiometer (plate method). Each experiment was carried out as follows.

Distilled water solutions at different concentrations were prepared for each of the test surfactants in 100 mL amounts. The mixtures were stirred until homogeneous solutions were obtained. The surface tensions of these solutions were then measured.

From the surface tension data, the area/molecule (area) at the interface and efficiency of adsorption were computed by use of the appropriate Gibb's Adsorption Equation:

$$\rho = \frac{-d\gamma}{d\log C_T} /2.303RT$$

where $\rho$=surface excess concentration (mol/cm$^2$)

$d\gamma$=change in surface or interfacial tension of the solvent (dyn·cm$^{-1}$)

$R=8.31\times10^7$ erg mol$^{-1}$ K$^{-1}$

C=molar concentration of solution

T=absolute temperature (°K)

pC-20 at the solution/air interface is defined as the negative logarithm of the surfactant concentration required to lower surface tension by 20 dyne/cm.

The results obtained for the surfactants alone are reported in Table 1.

Draves Wetting Test

The Draves Wetting Test is conducted according to ASTM D 2281-68. A solution of 500 ml, 0.1% by weight of the test surfactant were prepared. The resulting aqueous solution was poured into 500 ml graduate cylinder and 5 g of 100% cotton yarn weighted with 3 g hook was dropped into the cylinder. The time required for the yarn to sink to the bottom of cylinder was reported as Drave Wetting Time.

As used herein RHODAPEX® ESY is a sodium laurylether sulfate (1 EO); MIRANOL® H2M-SF is a salt free disodium lauroamphodipropionate; MIRANOL® CS is a sodium cocoamphohydroxypropyl sulphonate of the formula (Coco)-C(O)NHCH$_2$CH$_2$N(CH$_2$CH$_2$OH)CH$_2$CH (OH)CH$_2$SO$_3$Na; and MIRANOL® ULTRA is a cocoamphoacetate of the formula (Coco)-C(O)NHCH$_2$CH$_2$N (CH$_2$CH$_2$OH)CH$_2$CO$_2$Na. MIRANOL® CS, MIRANOL® H2M-SF, MIRANOL® JEM AND MIRANOL® ULTRA are amphoteric surfactants and RHODAPEX® ESY is an anionic surfactant. These materials are available from RhonePoulenc Specialty Chemicals Co.

The results obtained for the surfactants of Examples 3 and 4 alone as compared to two commercial non-gemini type surfactants are reported in Table 1 which follows:

TABLE 1

| SURFACE ACTIVITY UNBLENDED | | | | |
|---|---|---|---|---|
| Surfactant | CMC (M) | $\gamma_{cmc}$ | area (Å$^2$) | pC-20 |
| Product of EXAMPLE 3 (C$_{12}$ propionate) | 5.26*10$^{-6}$ | 39.5 | 80 | 6.3 |

TABLE 1-continued

SURFACE ACTIVITY UNBLENDED

| Surfactant | CMC (M) | $\gamma_{cmc}$ | area ($Å^2$) | pC-20 |
|---|---|---|---|---|
| pH 11, 0.1 M NaCl MIRANOL ® H2M-SF Lauroamphodipropionate | $6.6*10^{-5}$ | 33 | 49 | 5.1 |
| pH 11, 0.1 M NaCl Product of EXAMPLE 4 ($C_{12}$ sulphonate) | $6.7*10^{-6}$ | 32 | 70 | 6.6 |
| pH 11, 0.1 M NaCl MIRANOL ® CS Cocoamphosulfonate pH 11, 0.1 M NaCl | $4.0 \times 10^{-5}$ | 31 | 63 | 5.8 |

Hydrotropicity

Hydrotropicity was measured by determining the amount of surfactant needed to clarify a cloudy aqueous solution of 5% sodium hydroxide and 5% surfactant (IGEPAL® CO-630 -Nonylphenol ethoxylate - 9 moles EO). The results are expressed in weight percent of the aqueous solution. The lower the number, the greater the hydrotropicity. The results show that the product of Example 6 is over 60% more efficient than the conventional surfactant MIRANOL® JEM.

TABLE 2

| SURFACTANT | HYDROTROPICITY (Wt. %) |
|---|---|
| Product of Example 6 ($C_8$ PROPIONATE) | 0.3% |
| MIRANOL ® JEM (Sodium Mixed $C_8$ Amphocarboxylate) | 0.8% |

When the surface properties for the anionic $C_{12}$ propionate and $C_{12}$ sulfonate compounds of the invention (at the pH tested) are compared to the corresponding conventional anionic laurylamphodipropionate and cocoamphohydroxypropyl sulfonate (at the pHs tested) as shown in Table 1, the novel compounds of the invention show two unexpected surface active properties; unusually low critical micelle concentration (CMC) and $pC_{20}$ values in aqueous media. These properties are a measure of the tendency of the surfactant to form micelles and adsorb at the interface, and consequently, to reduce surface tension respectively. The values shown in Table 1 demonstrate that the $C_{12}$ propionates and sulfonates are one to two orders of magnitude (10-100 times) more efficient at reducing surface tension (pC-20) and more than one order of magnitude (or 10 times) more efficient at forming micelles. This unusually high surface activity for these molecules is a result of their unique structure; the presence of two optimally spaced hydrophobic chains and hydrophilic groups. This molecular structure provides energetically favorable decreases in the free energy of adsorption and micellization through favorable distortion of water structure, and, at the same time, providing a "close packed" arrangement at the interface. This is reflected by their relatively low area per molecule that's unexpected from the molecular dimensions for the molecule. The area per molecule for the compounds of the invention are comparable to corresponding conventional surfactants. The ability of the compounds of the invention to distort water structure through inhibition of crystalline or liquid crystalline phase formation in bulk phase and at the same time to pack closely on adsorption at the interface is contrary to conventional wisdom. This again demonstrates the uniqueness of the molecular design for these compounds which is very critical to providing unexpected exceptional surface and performance properties.

Exceptional surface activity and unique structural features for the compounds of the invention provide two other important performance properties that can have immense practical application in industry, i.e., their hydrotropicity, which is the ability of organic substances to increase the solubility of other insoluble organic substances in water, and solubilization, the dissolving of water insoluble organic compounds into aqueous surfactant solutions above their CMC levels. The compounds of the invention, because of their very low CMC values, are efficient solubilizers. This latter property will not only allow the formulation of homogeneous water insoluble materials, but also will enhance the surface activity of other surfactants whose low water solubility restrict their use. These novel surfactants of the invention are far better than comparable conventional surfactants in hydrotroping and solubilizing properties.

Because of their unusually high surface activity coupled with their hydrotropicity and solubilization properties, compounds of this invention will provide exceptionally high performance properties, at very low concentration, in practical applications such as detergency emulsification, solubilization, dispersancy, hydrotropicity, foaming and wetting. In addition, due to their extremely low monomer concentration at use levels, because of their extremely low CMC and $C_{20}$ values, two to one order less amount of the compounds of the invention than conventional surfactants can provide extremely low or no irritancy in personal care applications.

Surface Activities of Mixtures

The unusually high surface activity of the anionic surface active agents of the invention make them the surfactants of choice in enhancing the surface activity of mixtures containing other conventional zwitterionic, amphoteric, nonionic and cationic surfactants which can be significantly less surface active. The propionate and sulfonate compounds of the invention provide significant improvement in the surface activity of blends of these compounds with every other types of known surfactants unexpectedly when used in very small amounts. The improvement is beyond that can be calculated for the surfactant mixture and is considered synergistic. The results are shown in Table 2 as follows:

TABLE 2

| SURFACE ACTIVITIES of MIXTURES | | | | |
|---|---|---|---|---|
| SURFACTANT | CMC | $\gamma_{cmc}$ | area ($Å^2$) | pC-20 |
| PRODUCT OF EXAMPLE 3 (C12 Propionate) (pH 11, 0.1 M NaCL) With MIRANOL ® H2M-SF Disodium lauroamphodipropionate (25/75 mole ratio) | $1 \times 10^{-5}$ | 37 | 74 | 6.0 |

TABLE 3

| SURFACTANT | CMC | $\gamma_{cmc}$ | area ($Å^2$) | pC-20 |
|---|---|---|---|---|
| PRODUCT OF EXAMPLE 4 (C12 Sulphonate) | | | | |

TABLE 3-continued

| pH 11, 0.1 M NaCL With MIRANOL ® CS Sodium coco amphosulphonate (25/75 mole ratio) | $1.6 \times 10^{-5}$ | 32 | 66 | 6.2 |
|---|---|---|---|---|

As shown in Table 2, the compound of Example 3 ($C_{12}$ propionate) when blended with lauryl amphodipropionate, a comparable conventional amphoteric, at a 25/75 molar ratio provided at least 5–10 times improvement in surface activity, as measured by the reduction of CMC and pC-20 compared to the conventional anionics alone. Similar order of magnitude improvement in surface activity was obtained for a blend the compound of Example 4 ($C_{12}$ sulphonate) with a conventional anionic surfactant, cocoamphosulphonate (MIRANOL® CS) at the 25/75 molar ratio. This property of enhancement of surface activity and solubilization of blends when used in low concentrations can have wide applicability in industrial, personal care and pharmaceutical applications. The use of the compounds of the invention in combination with conventional surfactants can provide improved performance for blends even at significantly lower concentrations which is very desirable for both economic and environmental reasons. By virtue of these properties, these surfalctants can be combined with other conventional surfactants in very small amounts to dramatically improve surface activity and solubility of their blends. Thus these compositions have wide industrial applicability in significantly improving performance properties such as detergency, emulsion polymerization, emulsification, wetting, dispersancy and solubilization. Further this property of significantly lowering CMC and pC-20 values in mixtures containing other conventional surfactants should provide irritancy mitigating properties when used in combination with other more irritating surfac:tants, polymers and/or additives.

The unusually high surface activity also provides improved wetting as shown by the following Drave wetting times.

TABLE 4

Draves Wetting Time

| Product of EXAMPLE 3 ($C_{12}$ Propionate) 0.1 wt % Sol., pH 11 | Draves Wetting Time (sec) | |
|---|---|---|
| Surfactant (wt ratio) | MIRANOL ® H2M-SF | RHODAPEX ® ESY |
| 100/0 | >300 | >300 |
| 75/25 | 129 | 100 |
| 50/50 | 127 | 94 |
| 25/75 | 133 | 41 |
| 0/100 | >300 | 13 |

These properties of enhancement of surface activity, solubilization, and wetting of blends, even when used in small concentrations, can have a wide applicability in industrial, personal care, and pharmaceutical applications where the use of these compounds in combination with other conventional surfactants can provide improved performance for blends.

Although the subject invention has been described with respect to a preferred embodiment, it will be readily apparent to those having ordinary skill in the art to which the invention pertains that changes and modifications may be made thereto without departing from the spirit or scope of the subject invention as defined by the appended claims.

What is claimed is:

1. A cleaning composition comprising an aqueous solution having a cleaningly effective amount of a surfactant of the formula:

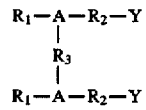

wherein $R_1$ represents $R_4$—B—$R_5$ wherein $R_4$ can be an alkyl or hydroxy substituted or perfluorinated alkyl of from 1 to about 22 carbon atoms and the hydroxy-substituted derivatives thereof; $R_5$ represents an alkylene group of 1 to 12 carbons and the hydroxy substituted derivatives thereof; B represents an amide group —C(O)N($R_6$)—, wherein $R_6$ independently represents a lower alkyl or hydroxy-substituted alkyl of from 1 to about 6 carbons or hydrogen; $R_2$ can independently represent a $C_1$ to about $C_{10}$ alkylene and the hydroxy-substituted derivatives thereof, an amide group —C(O)N($R_6$)—, a polyether group —($R_7$—O)$_x$ or $R_8$—$D_1$—$R_8$ wherein $R_6$ has been hereinbefore defined and $R_7$ independently represents a $C_2$ to about $C_4$ alkyl with x being a number between 1 and 20 and $R_8$ can independently be a $C_1$ to about $C_6$ alkylene and the hydroxy-substituted derivatives thereof and $D_1$ represents —O—, —S—, an amide group —C(O)N($R_6$)—, or —N($R_9$)— wherein $R_9$ independently represents a $C_1$ to about $C_{12}$ alkyl and the hydroxy-substituted derivatives thereof or hydrogen; $R_3$ can independently be an alkylene or alkylaryl of from 1 to about 10 carbon atoms and the hydroxy-substituted derivatives thereof or $R_{10}$—$D_2$—$R_{10}$ wherein $R_{10}$ can independently be an alkylene of from 1 to about 6 carbon atoms and the hydroxy-substituted derivatives thereof as well as aryl, and $D_2$ represents —O—, —S—, —$SO_2$—, a carbonyl group, a polyether group —O($R_7$—O)$_x$—, ($R_{11}$N($R_{11}$))$_z$ or aryl wherein $R_{11}$ represents a carbon chain of from 1 to about 12 carbon atoms and the hydroxy-substituted derivatives thereof or hydrogen, $R_7$ being as defined hereinabove with x being a number between about 1 and 20 and z is a number from 1 to about 4; "A" independently represents —N=and Y independently represents hydrogen, —$SO_3$H, —$OSO_3$H, —OP(O)(OH)$_2$, —P(O)(OH)$_2$, —COOH, —$CO_2$—$C_6H_4$—$SO_3$H and the salts thereof.

2. The cleaning composition of claim 1, wherein $R_2$ independently represents a lower alkylene of from 1 to about 4 carbon atoms.

3. The cleaning composition of claim 1, wherein $R_4$ is an alkyl of from about 6 to about 18 carbon atoms.

4. The cleaning composition of claim 3, wherein $R_5$ independently is an alkylene of from 2 to about 6 carbon atoms.

5. The cleaning composition of claim 4, wherein Y is sulfate, phosphate, carboxylate and the salts thereof.

6. The cleaning composition of claim 5, wherein said salt in Formula I is selected from the group consisting of an alkali metal salt, an alkaline earth metal salt, an ammonium salt, and an organic base salt.

7. The cleaning composition of claim 6, wherein said organic base salt is selected from the group consisting of monoethanolamine, diethanolamine, triethanolamine, triethylamine, trimethylamine and N-hydroxyethyl morpholine.

8. The cleaning composition of claim 5, wherein said salt in Formula I is an alkali metal salt.

9. The cleaning composition of claim 1, further comprising one or more additional surfactants selected from the group consisting of anionic, nonionic, cationic, and amphoteric surfactants and mixtures thereof.

10. The cleaning composition of claim 9, wherein said nonionic surfactant is selected from the group consisting of fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxethylene lanolin alcohols, polyoxyethylene fatty acid esters, polyoxyethylene glycerine fatty acids, polyoxyethylene propylene glycol fatty acid esters, a polyoxyethylene sorbitol fatty acid esters, polyoxyethylene castor oil or hardened castor oil derivatives, polyoxyethylene lanolin derivatives, polyoxethylene fatty acid amides, polyoxyethylene alkyl amines, alkyl pyrrolidones, glucamides, alkylpolyglucosides, mono- or dialkanol amides, polyoxyethylene alcohols, mono- or diamides, alkylamine oxides and mixtures thereof.

11. The cleaning composition of claim 9, wherein said anionic surfactant is selected from the group consisting of fatty acid soaps, ether carboxylic acids and the salts thereof, alkane sulfonate salts, α-olefin sulfonate salts, the sulfonate salts of a higher fatty acid ester, higher alcohol sulfate ester salts, fatty alcohol ether sulfate salts, higher alcohol phosphate ester salts, fatty alcohol ether phosphate ester salts, the condensates of higher fatty acids and amino acids, collagen hydrolysate derivatives and mixtures thereof.

12. The cleaning composition of claim 9, wherein said cationic surfactant is selected from the group consisting of alkyltrimethylammonium salts, dialkyl-dimethylammonium salts, alkyldimethylbenzylammonium salts, alkylpyridinium salts, alkylisoquinolinium salts, benzethonium chlorides, acylamino acid type cationic surfactants and mixtures thereof.

13. The cleaning composition of claim 9, wherein said amphoteric surfactant is selected from the group consisting of amino acids, betaines, sultaines, phosphobetaines, imidazoline-type amphoteric surfactants, soybean phospholipids, yolk lecithins and mixtures thereof.

14. The cleaning composition of claim 1, further comprising an auxiliary additive.

15. The cleaning composition of claim 14, wherein said auxiliary additive is selected from the group consisting of an inorganic salt such as Glauber salt and common salt, a builder, a humectant, a solubilizing agent, a UV absorber, a softener, a chelating agent, a bleach activator, a bleach stabilizer, and a viscosity modifier.

16. The cleaning composition of claim 1, wherein said compound of Formula I has the formula:

IV.

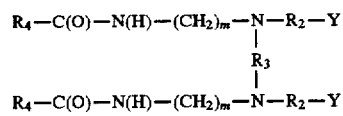

wherein $R_2$, $R_3$, $R_4$, and Y are as defined hereinbefore, and m represents a number between about 2 and about 10.

17. The cleaning composition of claim 1, wherein the solution is selected from the group consisting of hair shampoos, baby shampoos, body shampoos, bubble baths, bar soaps, bath gels, hair conditioning gels, skin creams and lotions, skin contacting cosmetics, make-up removal creams and lotions, liquid detergents, dish detergents, and liquid soaps.

18. The cleaning composition of claim 1, wherein the solution is selected from the group consisting of hard surface cleaners, emulsion polymerizers, laundry and dish detergents, liquid and bar soaps, carpet cleaners, lubricants, and metal cleaners.

19. The cleaning composition of claim 9, wherein the solution is selected from the group consisting of hair shampoos, baby shampoos, body shampoos, bubble baths, bar soaps, bath gels, hair conditioning gels, skin creams and lotions, skin contacting cosmetics, make-up removal creams and lotions, liquid detergents, dish detergents, and liquid soaps.

20. The cleaning composition of claim 9, wherein the solution is selected from the group consisting of hard surface cleaners, emulsion polymerizers, laundry and dish detergents, liquid and bar soaps, carpet cleaners, lubricants, and metal cleaners.

21. The cleaning composition of claim 16, wherein the solution is selected from the group consisting of hair shampoos, baby shampoos, body shampoos, bubble baths, bar soaps, bath gels, hair conditioning gels, skin creams and lotions, skin contacting cosmetics, make up removal creams and lotions, liquid detergents, dish detergents, and liquid soaps.

22. The cleaning composition of claim 16, wherein the solution is selected from the group consisting of hard surface cleaners, emulsion polymerizers, laundry and dish detergents, liquid and bar soaps, carpet cleaners, lubricants, and metal cleaners.

* * * * *